(12) United States Patent
Assmann et al.

(10) Patent No.: US 9,107,566 B2
(45) Date of Patent: Aug. 18, 2015

(54) MEASURING DEVICE AND MAGNETIC RESONANCE DEVICE COMPRISING A MEASURING DEVICE

(75) Inventors: Bernd Assmann, Fürth (DE); Michael Frank, Erlangen (DE); Sven Heggen, Erlangen (DE); Ernst Mustafa, Fürth (DE); Jürgen Rössler, Erlangen (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 0 days.

(21) Appl. No.: 13/449,344

(22) Filed: Apr. 18, 2012

(65) Prior Publication Data

US 2012/0271153 A1    Oct. 25, 2012

(30) Foreign Application Priority Data

Apr. 21, 2011   (DE) .......................... 10 2011 007 861

(51) Int. Cl.
| | | |
|---|---|---|
| A61B 5/055 | (2006.01) | |
| A61B 7/00 | (2006.01) | |
| A61B 5/00 | (2006.01) | |
| G01R 33/567 | (2006.01) | |

(52) U.S. Cl.
CPC .................. *A61B 7/00* (2013.01); *A61B 5/0017* (2013.01); *A61B 5/055* (2013.01); *G01R 33/5673* (2013.01); *A61B 5/7285* (2013.01); *A61B 2562/0204* (2013.01); *A61B 2562/0233* (2013.01)

(58) Field of Classification Search
CPC ....................................................... A61B 5/055
USPC .......................... 600/407, 410, 418, 425, 428
See application file for complete search history.

(56) References Cited

U.S. PATENT DOCUMENTS

| | | | | |
|---|---|---|---|---|
| 5,107,846 | A * | 4/1992 | Atlas .............................. | 600/479 |
| 6,771,999 | B2 * | 8/2004 | Salla et al. .................... | 600/413 |
| 2003/0036693 | A1 * | 2/2003 | Avinash et al. ............... | 600/413 |
| 2004/0116969 | A1 * | 6/2004 | Owen et al. ....................... | 607/6 |
| 2011/0098555 | A1 * | 4/2011 | Zenge .......................... | 600/411 |

FOREIGN PATENT DOCUMENTS

DE     102009050663 A1     4/2011

OTHER PUBLICATIONS

Maderwald S., et.al.; "Tesla Cardiac Imaging with a Phonocadiogram Trigger Device", at:: 19th Annual Meeting and Exhibition ISMRM 2011, Montreal, Canada, May 2011, pp. 41; Others; 2011.
German Search Report, Feb. 1, 2012, pp. 1-7.

* cited by examiner

*Primary Examiner* — Peter Luong

(57) ABSTRACT

A measuring device is provided. The measuring device has at least one sensor unit for capturing a cardiac signal, a postprocessing unit and a signal transfer unit for signal transfer between the at least one sensor unit and the postprocessing unit. The at least one sensor unit has at least one acoustic sensor element.

8 Claims, 2 Drawing Sheets

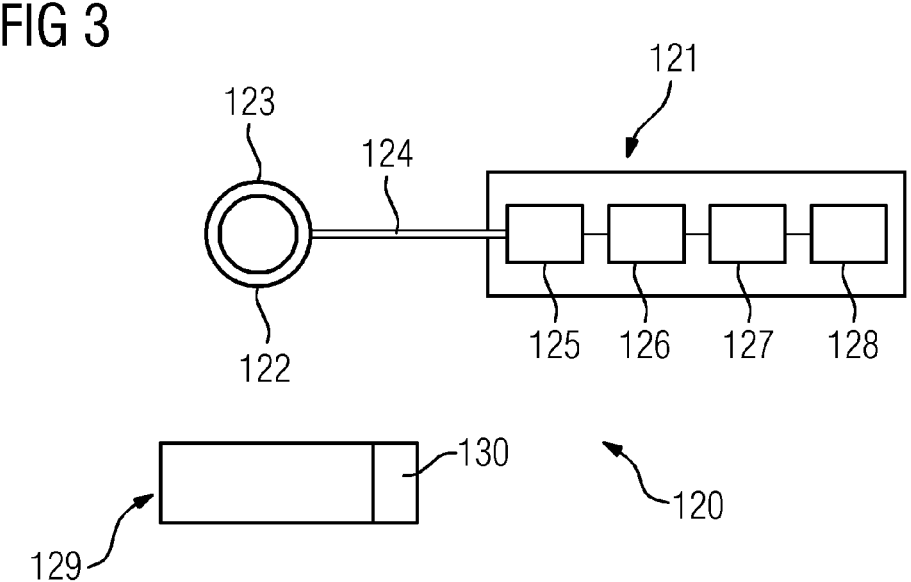
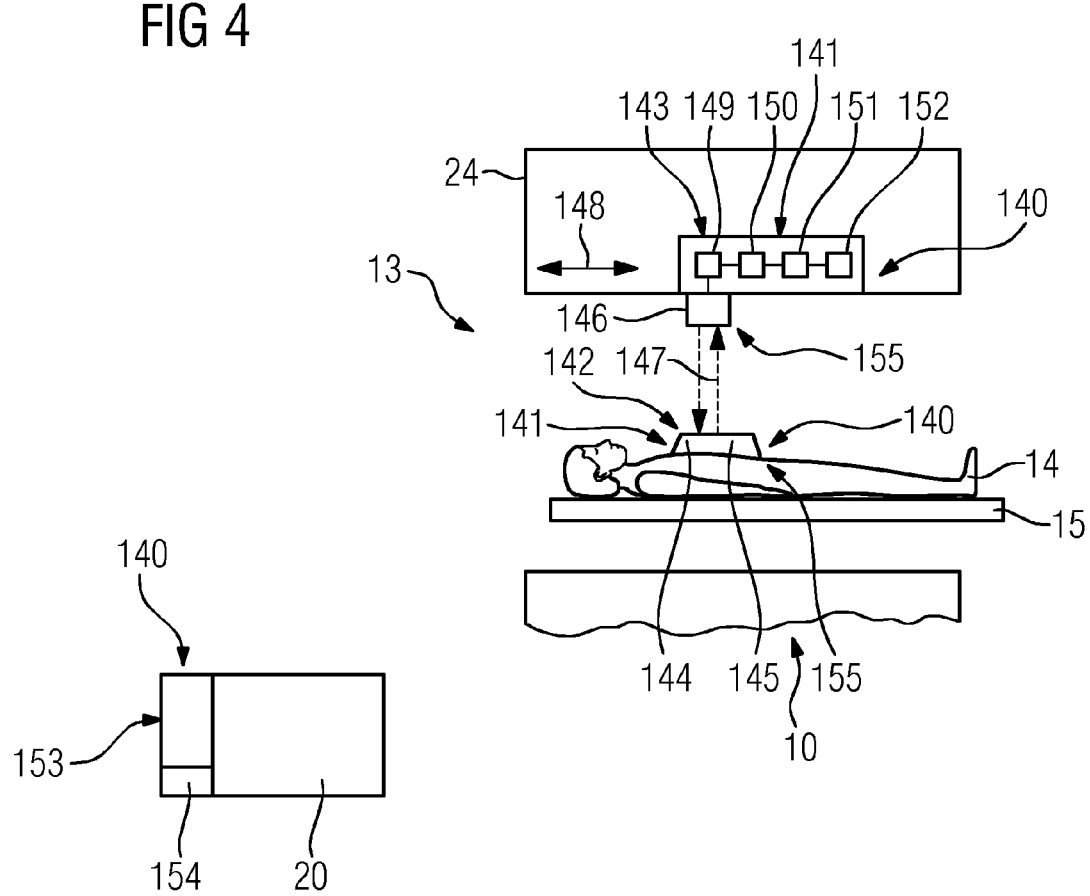

MEASURING DEVICE AND MAGNETIC RESONANCE DEVICE COMPRISING A MEASURING DEVICE

CROSS REFERENCE TO RELATED APPLICATIONS

This application claims priority of German application No. 10 2011 007 861.4 filed Apr. 21, 2011, which is incorporated by reference herein in its entirety.

FIELD OF INVENTION

The present invention relates to a measuring device comprising at least one sensor unit for capturing a cardiac signal, a postprocessing unit and a signal transfer unit for transferring signals between the at least one sensor unit and the postprocessing unit.

BACKGROUND OF INVENTION

In order to provide cardiac imaging for a patient, an imaging device (such as a magnetic resonance device in particular) must be synchronized with a cardiac signal of the patient. An ECG measuring device which has a sensor unit for capturing cardiac signals is customarily used for this purpose. The sensor unit comprises a plurality of ECG electrodes, which are placed on the patient in the chest region. A trigger signal for the cardiac imaging is then generated on the basis of the ECG signals that are captured.

SUMMARY OF INVENTION

The present invention addresses in particular the problem of providing a measuring device which allows a magnetic resonance measurement that is free of influences from an external magnetic field. The problem is solved by the features in the independent claims. Advantageous embodiments are described in the dependent claims.

The invention takes as its staring point a measuring device comprising at least one sensor unit for capturing a cardiac signal, a postprocessing unit and a signal transfer unit for transferring signals between the at least one sensor unit and the postprocessing unit.

It is proposed that the at least one sensor unit should feature at least one acoustic sensor element. This advantageously allows the detection of cardiac sounds free of influences from an external magnetic field, such as e.g. the magnetic field that is generated by the magnetic resonance device. It is therefore possible to capture cardiac signals, in particular acoustic cardiac signals and/or cardiac sounds, during a magnetic resonance examination without adversely affecting the patient, e.g. without the undesirable induction of currents and/or voltages in an ECG sensor unit as a result of applying a primary magnetic field and/or temporarily applying gradient fields. In this context, an acoustic sensor element is understood in particular to be a sensor element that is configured exclusively to detect sound-waves of acoustic signals, in particular acoustic cardiac sounds and/or cardiac noises. A detection range of the acoustic sensor element preferably encompasses a frequency range of the cardiac sounds and/or cardiac noises of humans. In this case, a maximal frequency of the cardiac sounds and/or cardiac noises of humans lies within a range of ±20 Hz relative to an average maximal frequency of 80 Hz, and most preferably within a range of ±10 Hz relative to the average maximal frequency of 80 Hz.

A particularly advantageous detection of cardiac noises and/or cardiac sounds while avoiding any interference caused by the applied magnetic field of the magnetic resonance device can be achieved if the at least one acoustic sensor device comprises at least one optical microphone. An optical microphone is understood to be in particular a microphone which is metal-free and/or cannot be magnetized, which detects acoustic signals such as e.g. cardiac sounds and/or cardiac noises by means of an optical signal and/or acoustically by means of a membrane, and which generates an optical signal for onward transfer, in particular a light signal and/or a laser signal that corresponds to the acoustic signal. In this context, the optical microphone can feature a membrane for the purpose of detecting the acoustic signals, or the detection can take place without a membrane in the optical microphone by capturing a frequency modulation and/or an amplitude modulation of a pulsed light beam.

It is further proposed that the at least one acoustic sensor element should comprise at least one sound-absorbing membrane, whereby an advantageous selection and/or amplification of the cardiac sounds can be achieved during the acoustic detection. The membrane preferably takes the form of a vibration membrane, whose resonance range or natural frequencies correspond at least partly to a frequency range of the cardiac sounds and/or the cardiac noises, which exhibit an average maximal frequency of approximately 80 Hz. Moreover, the sound-absorbing membrane can be arranged in an optical microphone and/or a receive unit of a stethoscope, wherein the receive unit of the stethoscope is in contact with the chest of the patient, in particular a chest region that covers the heart region, for the purpose of detecting the acoustic cardiac signals.

In an advantageous development of the invention, it is proposed that the at least one sensor unit should comprise a light-beam unit, which generates a laser beam that is reflected at the sound-absorbing membrane. In this type of configuration, the acoustic cardiac signal (in particular the cardiac sound) can be converted into an optical signal by means of the reflected laser beam, thereby allowing onward transfer of the detected signal with a minimum of interference. It is moreover possible to dispense with cables for transport and/or onward transfer of the laser beam, thereby increasing the reliability of the measuring device for cardiac signal measurement by preventing interruptions due to cable damage.

In a further embodiment of the invention, it is proposed that the measuring device should comprise at least one signal conversion unit, which converts a signal that has been captured by the at least one sensor element into an electrical signal. Advantageous postprocessing of the detected cardiac sounds can be performed within an electronic evaluation system on the basis of the electrical signals. The signal conversion unit can comprise e.g. a photodiode which converts optical signals into electrical signals, a pressure sensor that converts acoustic signals into electrical signals and/or further sensors and/or units that are considered to be suitable by a person skilled in the art.

It is further proposed that the at least one sensor unit should comprise a sound transport unit for the purpose of signal transfer between the at least one acoustic sensor element and the signal conversion unit. As a result, the detected acoustic signal can advantageously be protected against in particular acoustic interfering signals during its transfer to the signal conversion unit, and superimposition of the detected acoustic signal by acoustic interfering signals can be prevented. In this type of configuration, the signal conversion unit preferably features a pressure sensor, which converts the sound-waves arriving at the pressure sensor into electrical signals in particular. In this context, a sound transport unit is understood to be in particular a unit that features e.g. a tube which is filled with a sound propagation medium (in particular air) and which transfers or transports sound-waves of an acoustic signal (in particular cardiac noises and/or cardiac sounds) selectively to a target location while protecting them from interfering signals.

It is further proposed that the signal transfer unit should be configured for wireless signal transfer between the at least one sensor unit and the postprocessing unit. It is thereby advantageously possible to dispense with long cables that would otherwise be required for a connection between the at least one sensor unit and the postprocessing unit for the purpose of signal interchange and/or data interchange, and consequently also to prevent failures of the cardiac signal measurement due to cable fractures. It is therefore also possible in particular to avoid hindrances that are provoked and/or caused as a result of cable connections (such as jamming of connection cables when transporting the patient in particular), and thus advantageously to increase reliability and in particular service life of the at least one sensor unit and/or the measuring device. In this context, a wireless signal transfer is understood to be in particular a signal transfer without cables, by means of which information (in particular a characteristic value of the detected cardiac sounds) is interchanged and/or transferred via electromagnetic waves.

In a further embodiment of the invention, it is proposed that the at least one sensor unit should take the form of a mobile sensor unit, and that a light-beam unit and/or the signal conversion unit should be arranged within the mobile sensor unit. A particularly compact sensor unit can be provided, having in particular short paths between the at least one sensor element and the light-beam unit and/or the signal conversion unit. This also allows simple operation of the at least one sensor unit due to the compact nature of the sensor unit.

It is further proposed that the at least one sensor unit should comprise a partial region that is arranged on a housing of a magnetic resonance device, and that a light-beam unit and/or the signal conversion unit should be arranged within said partial region. It is thereby advantageously possible to achieve a connection (in particular a wireless connection) between the at least one sensor element, which is preferably in contact with the patient, and the light-beam unit. As a result of arranging the light-beam unit on the housing, it is possible to capture a relative vibrational movement of e.g. a membrane in relation to the light-beam unit, and an acoustic cardiac sound can be determined thus.

A particularly advantageous adaptation of a position of the light-beam unit to a position (in particular a heart position) of the patient can be achieved if the light-beam unit is so arranged as to be movable along at least one direction within the partial region. Said direction is preferably parallel with a longitudinal direction of a holding region for holding the patient.

If the at least one sensor unit is so designed as to be magnetic resonance-compatible, the measuring device can advantageously be used to trigger magnetic resonance imaging.

Furthermore, the invention takes as its starting point a magnetic resonance device comprising a measuring device, wherein a trigger signal for magnetic resonance imaging is generated by means of the measuring device.

It is proposed that the magnetic resonance device should comprise a holding region for holding a patient and a housing that surrounds the holding region, wherein a light-beam unit of the measuring device is arranged on the housing that surrounds the holding region. As a result of the arrangement of the light-beam unit on the housing that surrounds the holding region, it is advantageously possible to capture an acoustic cardiac sound by capturing a relative vibrational movement of a membrane relative to the light-beam unit. A particularly advantageous capture of the acoustic heart sound due to optimal positioning of the light-beam unit relative to a heart region of the patient can be achieved if the light-beam unit is arranged on the housing which surrounds the holding region in such a way that it can be moved along at least one direction.

In a further embodiment of the invention, it is proposed that the magnetic resonance device should feature a primary magnet for generating a primary magnetic field, and that a postprocessing unit of the measuring device should be arranged outside of a region that is penetrated by the primary magnetic field. The postprocessing unit, in particular a computing unit of the postprocessing unit, can advantageously be protected against any adverse effect from the magnetic field.

BRIEF DESCRIPTION OF THE DRAWINGS

Further advantages, features and details of the invention are derived from the exemplary embodiments that are described below and with reference to the drawings, in which:

FIG. 3 shows a second exemplary embodiment of the inventive measuring device, and FIG. 4 shows a third exemplary embodiment of the inventive measuring device.

DETAILED DESCRIPTION OF INVENTION

Figure 1:
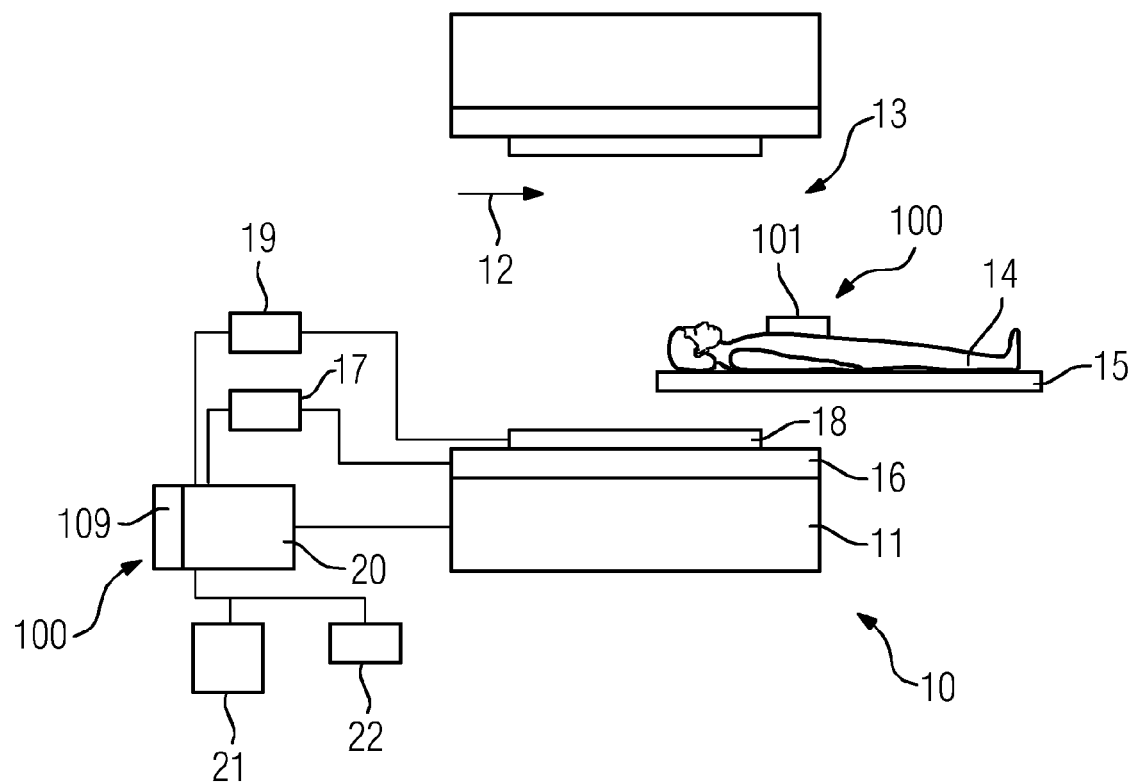
FIG. 1 shows a schematic illustration of a magnetic resonance device comprising a measuring device according to the invention.

FIG. 1 shows a magnetic resonance device 10 according to the invention. The magnetic resonance device 10 comprises a primary magnet 11 for generating a strong and in particular constant primary magnetic field 12. Moreover, the magnetic resonance device 10 comprises a cylindrical holding region 13 for holding a patient 14, wherein the holding region 13 is surrounded by the primary magnet 11 in a circumferential direction. The patient 14 can be pushed into the holding region 13 by means of a patient couch 15 of the magnetic resonance device 10.

The magnetic resonance device 10 additionally features a gradient coil 16 for generating magnetic field gradients that are used for spatial encoding during imaging. The gradient coil 16 is controlled by means of a gradient control unit 17. Furthermore, the magnetic resonance device 10 features high-frequency antennas 18 and a high-frequency antenna unit 19 for exciting a polarization which occurs in the primary magnetic field 12 that is generated by the primary magnet 11. The high-frequency antennas 18 are controlled by the high-frequency antenna unit 19 and beam high-frequency magnetic resonance sequences into an examination space that is essentially formed by the holding region 13. The magnetization is thereby deflected from its position of equilibrium. The high-frequency antenna unit 19 is also used to receive magnetic resonance signals.

The magnetic resonance device 10 features a control unit 20 for controlling the primary magnet 11, the gradient control unit 17 and the high-frequency antenna unit 19. The control unit 20 controls the magnetic resonance device 10 centrally, e.g. by executing a predefined imaging gradient echo sequence. Control information (such as e.g. imaging parameters) and reconstructed magnetic resonance images can be displayed on a display unit 21 (e.g. a monitor) of the magnetic resonance device 10. The magnetic resonance device 10 additionally features an input unit 22, by means of which the information and/or parameters can be entered by an operator during a measurement operation.

The illustrated magnetic resonance device 10 can obviously comprise further components which are normally featured in magnetic resonance devices 10. Moreover, the way in which a magnetic resonance device 10 generally functions is also known to a person skilled in the art, and therefore a detailed description of the general components has been omitted.

Figure 2:
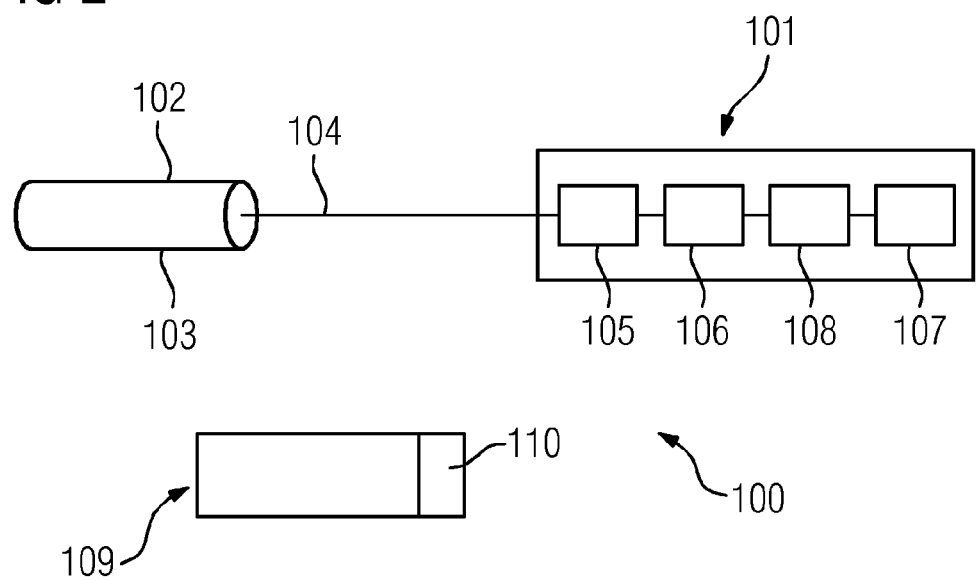
FIG. 2 shows a first exemplary embodiment of the inventive measuring device having an optical microphone.

The magnetic resonance device 10 additionally features a measuring device 100 as illustrated in greater detail in the FIGS. 2 to 4. The measuring device 100 is used to capture acoustic cardiac signals and/or cardiac sounds, which are then used to generate a trigger signal for synchronization of the magnetic resonance device 10 with the heartbeat of the patient 14, thereby ensuring an exact timing of the medical imaging with the heartbeat for the magnetic resonance imaging.

FIG. 2 schematically illustrates a first exemplary embodiment of the measuring device 100 according to the invention. The measuring device 100 is designed to capture and/or detect cardiac signals, and has a sensor unit 101 with an acoustic sensor element 102 for this purpose. In an alternative embodiment, the measuring device 100 can also have more than one sensor unit 101 and/or the sensor unit 101 can have two or more acoustic sensor elements 102. In order to allow error-free measuring operation of the magnetic resonance device 10 in conjunction with the measuring device 100, the sensor unit 101 of the measuring device 100 is so designed as to be magnetic resonance-compatible.

The acoustic sensor element 102 in the present exemplary embodiment takes the form of an optical microphone 103 and is intended for acoustic detection of cardiac sounds of the patient 14. In this case, the optical microphone 103 can comprise a sound-absorbing membrane, this being situated on a chest region of the patient 14 for detection of cardiac sounds. The membrane can also have a reflective coating. Furthermore, the optical microphone 103 can have a light-beam unit which comprises a light-emitting diode. The optical microphone 103 can include an optical-fiber cable which is situated between the light-emitting diode and the membrane, and which directs a light from the light-emitting diode directly onto the membrane. During operation of the optical microphone 103 with membrane, a light beam and/or optical signal that was generated by the light-beam unit is at least partially reflected at the membrane due to the reflective coating of the membrane, and a further optical signal, which is formed by the reflected optical signal, is carried from the membrane to a signal conversion unit 105 via an optical-fiber cable 104 of the sensor unit 101. When detecting cardiac sounds in this type of configuration, the membrane moves as a result of sound-waves, such that the beam which is reflected during movement of the membrane is phase-shifted when it hits a light inlet opening of the further optical-fiber cable 104 relative to a beam that is reflected during a still state of the membrane, and therefore a smaller light component can be coupled into the further optical-fiber cable 104 for carrying away the reflected light. In this way, an optical signal for onward transfer of the cardiac signal is generated by means of the acoustically detected cardiac signals at the membrane.

Alternatively, the optical microphone 103 can also be designed such that it does not have a membrane, it being possible in this context to take advantage of the effect that a pulsed light beam can be modulated in its frequency and/or amplitude by sound, in particular when a sound field is traversed. In this context, the sound-waves of the cardiac sounds can be determined by capturing a change in the amplitude and/or the frequency of the pulsed light beam relative to a reference beam. Onward transfer of the captured signals to a signal conversion unit 105 is also possible by means of at least one optical-fiber cable 104.

The signal conversion unit 105 of the sensor unit 101 takes the form of a photodiode. For the purpose of capturing the cardiac sounds, the optical signals that are carried away from the optical microphone 103 via the optical-fiber cable 104 hit the photodiode. Electrical signals are generated depending on an intensity of the optical signals hitting the photodiode, wherein said electrical signals can differ in respect of at least one signal parameter (e.g. a current strength and/or a voltage, etc.), which is dependent on the intensity of the optical signals that arrive. These different electrical signals therefore represent the different intensities of the light hitting the photodiode and hence the sound-waves of the cardiac sounds that are emitted by the heart of the patient 14. An alternative embodiment of the signal conversion unit 105 is easily conceivable.

Furthermore, the sensor unit 101 comprises a signal filter unit 106, an analog-digital conversion unit 108 and a signal transfer unit 107. The electrical signal that is generated by the photodiode is carried to the signal filter unit 106 of the sensor unit 101, where it is at least partially separated from interfering signals and/or noise. The signal is then passed to the analog-digital conversion unit 108 within the sensor unit 101 and a digital signal is generated.

The measuring device 10 additionally comprises a postprocessing unit 109. An output signal of the analog-digital conversion unit 108 is transferred to the signal transfer unit 107, which is designed for wireless signal transfer between the sensor unit 101 and the postprocessing unit 109. For this purpose, the electrical signals are transmitted to the postprocessing unit 109, which has a signal receiving unit 110. The signal interchange between the signal transfer unit 107 and the postprocessing unit 109 is achieved by emission and/or transfer electromagnetic waves. Alternatively, the transmitted signals can also comprise analog signals.

The postprocessing unit 109 comprises a computing unit, in which is stored the software and/or computer programs that are required for analysis of the captured signals, wherein said software and/or computer programs further process the signals that are captured and prepared by the sensor unit 101. In this context, the signals are prepared inter alia for the purpose of generating a trigger signal for the magnetic resonance device 10, such that synchronization of the magnetic resonance imaging with the trigger signal for a magnetic resonance measurement can take place. The postprocessing unit 109 of the measuring device 100 is connected to the control unit 20 of the magnetic resonance device 10 via a data interchange unit (not shown in further detail). Alternatively, it is also possible for the postprocessing unit 109 of the measuring device 100 to be integrated into the control unit 20 of the magnetic resonance device 10. The postprocessing unit 109 is so arranged as to be outside of the holding region 13 and also outside of a region that is penetrated by the primary magnetic field 12. The postprocessing unit 109 can also comprise further units and/or components such as a storage unit, for example.

The sensor unit 101 takes the form of a mobile sensor unit 101 which is connected wirelessly and/or without cables to the postprocessing unit 109 and/or further units of the measuring device 100 for a measurement operation. The mobile sensor unit 101 comprising the acoustic sensor element 102, the signal conversion unit 105, the signal filter unit 106, the analog-digital conversion unit 108 and the signal transfer unit 107 is placed onto a chest region of the patient 14, wherein the acoustic sensor element 102 is in contact with a chest region that covers a heart region of the patient 14.

FIGS. 3 and 4 show alternative exemplary embodiments of the measuring device 120 and 140 respectively. The following description is essentially limited to the differences relative to the exemplary embodiment in FIG. 2, wherein reference is made to the description of the exemplary embodiment in FIG. 2 in respect of components, features and functions that remain the same.

FIG. 3 shows an embodiment of an inventive measuring device 120 as an alternative to the description relating to FIG. 2. The measuring device comprises a mobile sensor unit 121 having an acoustic sensor element 122. The acoustic sensor element 122 comprises a chest element 123 of a stethoscope with a sound-absorbing membrane. The sensor unit 121 additionally comprises a sound transport unit 124 in the form of an air tube, which transfers the acoustic signal of the cardiac sounds captured by the membrane to a signal conversion unit 125 of the sensor unit 121. The cardiac sounds and/or soundwaves captured by the membrane are passed from the membrane to the sound transport unit 124 and transported onward by propagation of the sound-waves within the air tube.

The signal conversion unit 125 comprises a pressure sensor that converts the incoming sound-waves into an electrical signal, wherein the electrical signal generated by the pressure sensor is dependent on a frequency and/or a pressure and/or an amplitude of the sound-waves. The pressure sensor can take the form of a differential pressure sensor and/or other pressure sensors that are considered to be suitable by a person skilled in the art.

In a similar manner to the description for FIG. 2, the electrical signal is passed from the signal conversion unit 125 to a signal filter unit 126 and an analog-digital conversion unit 127 for generating a digital electrical signal. The digital electrical signal is then transmitted via a signal transfer unit 128 wirelessly and/or without cables to a postprocessing unit 129, which has a receive unit 130 for this purpose, of the measuring device 120. In this case, an arrangement and functionality of the postprocessing unit 129 within the magnetic resonance device 10 corresponds to an arrangement and functionality of the postprocessing unit 109 in the exemplary embodiment as per FIG. 2.

FIG. 4 shows an embodiment of an inventive measuring device 140 as an alternative to the description relating to FIGS. 2 and 3. The measuring device 140 comprises a sensor unit 141 which has a mobile partial region 142 and a partial region 143 that is arranged on a housing 24 of the magnetic resonance device 10. The mobile partial region 142 of the sensor unit 141 comprises an acoustic sensor element 144, which features a sound-absorbing membrane 145. The membrane is in contact with a chest region of the patient 14, which covers a heart region of the patient 14, for the purpose of capturing the cardiac sounds.

The partial region 143 that is arranged on the housing 24 of the magnetic resonance device 10 comprises a light-beam unit 146, which takes the form of a laser unit and generates a laser beam 147. The laser beam 147 is reflected at the membrane 145 in order to capture the cardiac sounds of the patient 14. During detection of acoustic cardiac signals, the membrane 145 is caused to vibrate and therefore executes a movement relative to the laser unit, this being mounted securely on the housing 24 of the magnetic resonance device 10 in order to perform a measurement. Due to a varying distance between the laser unit and the membrane due to vibrations of the membrane 145, the reflected laser beam 147 can be modulated in respect of at least one laser beam parameter, such as e.g. its phase and/or frequency. In order to allow effective capture of the cardiac sounds, at least the laser unit is movably arranged on one side of the housing 24 that surrounds the holding region 13 of the magnetic resonance device 10, said side being oriented towards the holding region 13, wherein the laser unit is mounted on the wall 24 in such a way that it can be moved along a direction 148. The direction 148 is so aligned as to be parallel with a longitudinal direction of the holding region 13. In this way, a position of the laser unit can be adapted to a position of the patient 14 for the purpose of cardiac imaging. Alternatively, the whole of the partial region 143 which is part of the sensor unit 101 and is arranged on the housing 24 can be so mounted on the housing 24 as to be movable along the direction 148. The acoustic sensor element 144 (with membrane) and the laser unit together form an optical microphone 155.

The reflected laser beam 147 is detected by the laser unit and is forwarded to a signal conversion unit 149 of the sensor unit 141. As described in relation to FIG. 2, the signal conversion unit 149 takes the form of a photodiode which converts the optical signal into an electrical signal whose parameters (in particular a current strength and/or a voltage) are dependent on the signal parameters of the detected laser signal. The electrical signal is then passed to a signal filter unit 150 and an analog-digital conversion unit 151 as described in relation to FIG. 2. The digital electrical signal is then passed to a signal transfer unit 152, which is designed to transmit the digital electrical signals to a postprocessing unit 153 of the measuring device 140 wirelessly and/or without cables. The postprocessing unit 153 has a receive unit 154 for this purpose. In addition to the laser unit, the partial region 143 which is part of the sensor unit 141 and is arranged on the housing 24 of the magnetic resonance device 10 comprises the signal conversion unit 149, the signal filter unit 150, the analog-digital conversion unit 151 and the signal transfer unit 152.

In this case, an arrangement and functionality of the postprocessing unit 153 within the magnetic resonance device 10 corresponds to an arrangement and functionality of the postprocessing unit 109 in the exemplary embodiment as per FIG. 2. Alternatively, the postprocessing unit 153 can also be arranged directly adjacent to the sensor unit 141 and/or the signal transfer unit 152 can have a data transfer cable for transferring the digital electrical signals between the sensor unit 141 and the postprocessing unit 153.

The invention claimed is:

1. A magnetic resonance device to be used in a magnetic resonance examination, comprising:
a housing that surrounds a holding region for holding a patient; and
an optical microphone for capturing and processing an acoustic cardiac signal of the patient and sending out an output signal,
wherein the measuring device is mounted on an inner side wall of the housing towards the holding region within a magnetic field generated by the magnetic resonance device.

2. The magnetic resonance device as claimed in claim 1, wherein the an optical microphone comprises a photodiode for converting the acoustic cardiac signal into an electrical signal.

3. The magnetic resonance device as claimed in claim 1, further comprising a computer for postprocessing the output signal.

4. The magnetic resonance device as claimed in claim 3, wherein the output signal are wirelessly transferred to the computer.

5. The magnetic resonance device as claimed in claim 3, wherein the computer is arranged outside a region that is penetrated by the magnetic field.

6. The magnetic resonance device as claimed in claim 1, wherein the an optical microphone is movably mounted on the inner side wall of the housing.

7. The magnetic resonance device as claimed in claim 1, wherein the an optical microphone is magnetic resonance-compatible.

8. The magnetic resonance device as claimed in claim 1, wherein the an optical microphone generates a trigger signal for the magnetic resonance examination.

\* \* \* \* \*